(12) United States Patent
Hagemann

(10) Patent No.: US 11,514,501 B2
(45) Date of Patent: Nov. 29, 2022

(54) NAVIGATION METHOD, SYSTEM, AND COMPUTER PROGRAM PRODUCT BASED ON USER SPECIFICATION

(71) Applicant: INTERNATIONAL BUSINESS MACHINES CORPORATION, Armonk, NY (US)

(72) Inventor: Carsten Hagemann, Ashmore (AU)

(73) Assignee: International Business Machines Corporation, Armonk, NY (US)

(*) Notice: Subject to any disclaimer, the term of this patent is extended or adjusted under 35 U.S.C. 154(b) by 228 days.

(21) Appl. No.: 16/126,315

(22) Filed: Sep. 10, 2018

(65) Prior Publication Data
US 2020/0082457 A1 Mar. 12, 2020

(51) Int. Cl.
G06Q 30/00 (2012.01)
G06Q 30/06 (2012.01)
H04W 4/024 (2018.01)
G16H 70/20 (2018.01)
G06K 7/14 (2006.01)
H04L 67/52 (2022.01)
G06F 3/0482 (2013.01)
G06F 3/16 (2006.01)

(52) U.S. Cl.
CPC ....... G06Q 30/0633 (2013.01); G06K 7/1417 (2013.01); G06Q 30/0639 (2013.01); G16H 70/20 (2018.01); H04L 67/52 (2022.05); H04W 4/024 (2018.02); G06F 3/0482 (2013.01); G06F 3/167 (2013.01)

(58) Field of Classification Search
None
See application file for complete search history.

(56) References Cited

U.S. PATENT DOCUMENTS

| 9,811,840 B2 | 11/2017 | Sinclair | |
| 2005/0076158 A1* | 4/2005 | Kwon | G16H 10/60 710/1 |
| 2011/0225068 A1* | 9/2011 | Figueroa | G06F 16/29 701/533 |
| 2012/0310758 A1 | 12/2012 | Bai et al. | |
| 2014/0019300 A1 | 1/2014 | Sinclair | |
| 2014/0156450 A1 | 6/2014 | Ruckart et al. | |
| 2014/0207615 A1 | 7/2014 | Li et al. | |

(Continued)

OTHER PUBLICATIONS

Indunil, E.J.C., The best preferred product location recommendation according to user context and the preferences, Sep. 1, 2017, 2017 Seventeenth International Conference on Advances in ICT for Emerging Regions (ICTers), pp. 1-6 (Year: 2017).*

(Continued)

*Primary Examiner* — Jeffrey A. Smith
*Assistant Examiner* — Timothy J Kang
(74) *Attorney, Agent, or Firm* — Alexis N. Hatzis (57) ABSTRACT

A method, computer system, and a computer program product of providing digital navigation to a user on a user device is provided. The present invention may include communicating a plurality of navigation commands to the user for navigation within a store, wherein the plurality of navigation commands are generated in response to a user-scanned QR code at the store, and are based on a user-provided specification.

14 Claims, 6 Drawing Sheets

(56) References Cited

U.S. PATENT DOCUMENTS

| | | | |
|---|---|---|---|
| 2014/0351098 A1* | 11/2014 | Shafer | G06Q 10/087 |
| | | | 705/28 |
| 2015/0228004 A1* | 8/2015 | Bednarek | G06Q 10/08355 |
| | | | 705/26.8 |
| 2016/0071149 A1* | 3/2016 | Farshori | G06T 19/006 |
| | | | 705/14.51 |
| 2017/0186068 A1 | 6/2017 | Dumouchel et al. | |
| 2018/0040037 A1 | 2/2018 | Blair, II | |
| 2019/0087835 A1* | 3/2019 | Schwed | H04L 63/0414 |
| 2020/0005378 A1* | 1/2020 | Anderson | G06Q 30/0281 |

OTHER PUBLICATIONS

Mell et al., "The NIST Definition of Cloud Computing", Recommendations of the National Institute of Standards and Technology, NIST Special Publication 800-145, Sep. 2011, 7 pages.

Disclosed Anonymously, "Smarter Supermarket Way Finding", IP.com Prior Art Database Technical Disclosure, IP.com No. IPCOM000209828D, Publication Date: Aug. 17, 2011 pp. 1-4.

Disclosed Anonymously, "Method and System for Facilitating Allergy-Safe Shopping", IP.com Prior Art Database Technical Disclosure, IP.com No. IPCOM000235975D, Publication Date: April 1, 2014 pp. 1-2.

Disclosed Anonymously, "In Store Navigation Tool", IP.com Prior Art Database Technical Disclosure, IP.com No. IPCOM000237997D, Publication Date: Jul. 24, 2014, p. 1.

* cited by examiner

NAVIGATION METHOD, SYSTEM, AND COMPUTER PROGRAM PRODUCT BASED ON USER SPECIFICATION

BACKGROUND

The present invention relates generally to the field of computing, and more particularly to navigation systems.

Food allergies or intolerances are very common, however, even without a diagnosed allergy, many people desire to avoid certain food ingredients. For example, this may include avoiding artificial colorings, preservatives, or even gluten, among many other food components, based on a perceived impact on one's health. Grocery shoppers may face a challenge in finding food that is suitable, given the shoppers' dietary restrictions and concerns. A grocery shopper may determine what food to purchase by reading food labels on all products of a given food type located in the market in which the grocery shopper is shopping. Unfortunately, however, many food labels may be difficult to read and understand.

SUMMARY

Embodiments of the present invention disclose a method, computer system, and a computer program product for navigation based on user specification. The present invention may include communicating a plurality of navigation commands to the user for navigation within a store, wherein the plurality of navigation commands are generated in response to a user-scanned QR code at the store, and are based on a user-provided specification.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for navigation based on user specification. As such, the present embodiment has the capacity to improve the technical field of navigation systems by connecting to a store's inventory of items and determining, based on inputted user specifications, what items within the store will be a good match for the user. More specifically, the present invention may include communicating a plurality of navigation commands to the user for navigation within a store, wherein the plurality of navigation commands are generated in response to a user-scanned QR code at the store, and are based on a user-provided specification.

Food allergies or intolerances are very common, however, even without a diagnosed allergy, many people desire to avoid certain food ingredients. For example, this may include avoiding artificial colorings, preservatives, or even gluten, among many other food components, based on a perceived impact on one's health. Grocery shoppers may face a challenge in finding food that is suitable, given the shoppers' dietary restrictions and concerns. A grocery shopper may determine what food to purchase by reading food labels on all products of a given food type located in the market in which the grocery shopper is shopping. Unfortunately, however, many food labels may be difficult to read and understand.

Therefore, it may be advantageous to, among other things, implement a system whereby grocery shoppers may define a list of ingredients that they wish to avoid or that they wish to limit their intake of, in addition to defining a list of groceries that the grocery shopper may wish to purchase, so that once the grocery shopper enters a grocery store, the system may identify suitable items for the grocery shopper to purchase, based on the grocery shopper's predefined criteria, and may further provide a map of the shop's interior, highlighting the items that the grocery shopper desires to purchase along with the items' locations.

According to at least one embodiment, grocery shoppers may be navigated through a grocery store based on a predefined list consisting of items desired to be purchased and ingredients intent on avoiding, resulting in an improved shopping experience.

According to at least one embodiment, the described in-store navigation system based on user specification program may be utilized by any market which sells items of different variety. This may include, among other things, clothing stores selling garments which are made of different materials, and food stores selling food products which are made of different ingredients. As described previously with respect to food ingredients, a clothing shopper may define clothing materials which the shopper wishes to purchase or avoid, and the navigation system based on user specification program may provide a map of the clothing store's interior, highlighting garments that the shopper may desire to purchase along with the items' in-store locations. Garments that the shopper may desire to purchase may include garments that were included on the shopper's shopping list which do not contain the avoided materials.

According to at least one embodiment, a user may install the navigation system based on user specification program as an application on his or her mobile device or tablet, or may access a web-based version of the navigation system based on user specification program on any internet-connected device. The navigation system based on user specification program may also be accessed by a store desiring to participate in the navigation system based on user specification program. Once a store account within the navigation system based on user specification program is created, information pertaining to location of items within the store, including but not limited to aisle and/or shelf information, may be inputted by the store, or may be retrieved automatically by the navigation system based on user specification program once connected to the store's inventory database (i.e., database 114) of product information. Store information may also include an inventory of items sold by the store, including a detailed list of item ingredients as provided by an item's food label.

According to at least one embodiment, a user of the navigation system based on user specification program may define a maximum amount of a food ingredient that may be contained within a single food item. For example, if a maximum amount is equal to '0' this may indicate to the navigation system based on user specification program that the user wishes to avoid the ingredient completely. A user of the navigation system based on user specification program may alternatively, or additionally, define a type of item or food group that the user desires to purchase (e.g., fruit, vanilla yogurt and/or tomato sauce, among other items).

According to at least one embodiment, when a user of the navigation system based on user specification program enters a store, which has an inventory logged with the navigation system based on user specification program, the specifications (i.e., conditions) previously inputted by the user may be reviewed together with the store's inventory, and items sold by the store may be added to or removed from the user's shopping list based on the user's defined criteria (e.g., allergies and/or preferred alternatives). For example, the navigation system based on user specification program will review the store's inventory and will generate a shopping list (i.e., a purchase list) for the user based on the specifications inputted by the user, which may include but are not limited to including desired food items and allergies.

According to at least one embodiment, the navigation system based on user specification program may combine lists generated by the user within the user's personal account with food items available for purchase in the store. First, the navigation system based on user specification program may select items within the store that the user has specifically indicated a desire to purchase, adding the selected items to a "Shopping List" within the navigation system based on user specification program. The navigation system based on user specification program may then go through all remaining items on the inventory of items available for purchase within the store, and may remove from purchase those items which contain ingredients that the user wishes to avoid, or which contain ingredients in higher amount than desired by the user.

According to at least one embodiment, after narrowing down the inventory of items, the navigation system based on user specification program may generate a list of items for purchase by the user. The navigation system based on user specification program may then send a map and locations of the items for purchase to the user's mobile device or tablet, and may further use in-store audio and visual navigation within the navigation system based on user specification program interface to guide the user through the store to the location of each desired item.

Figure 1:
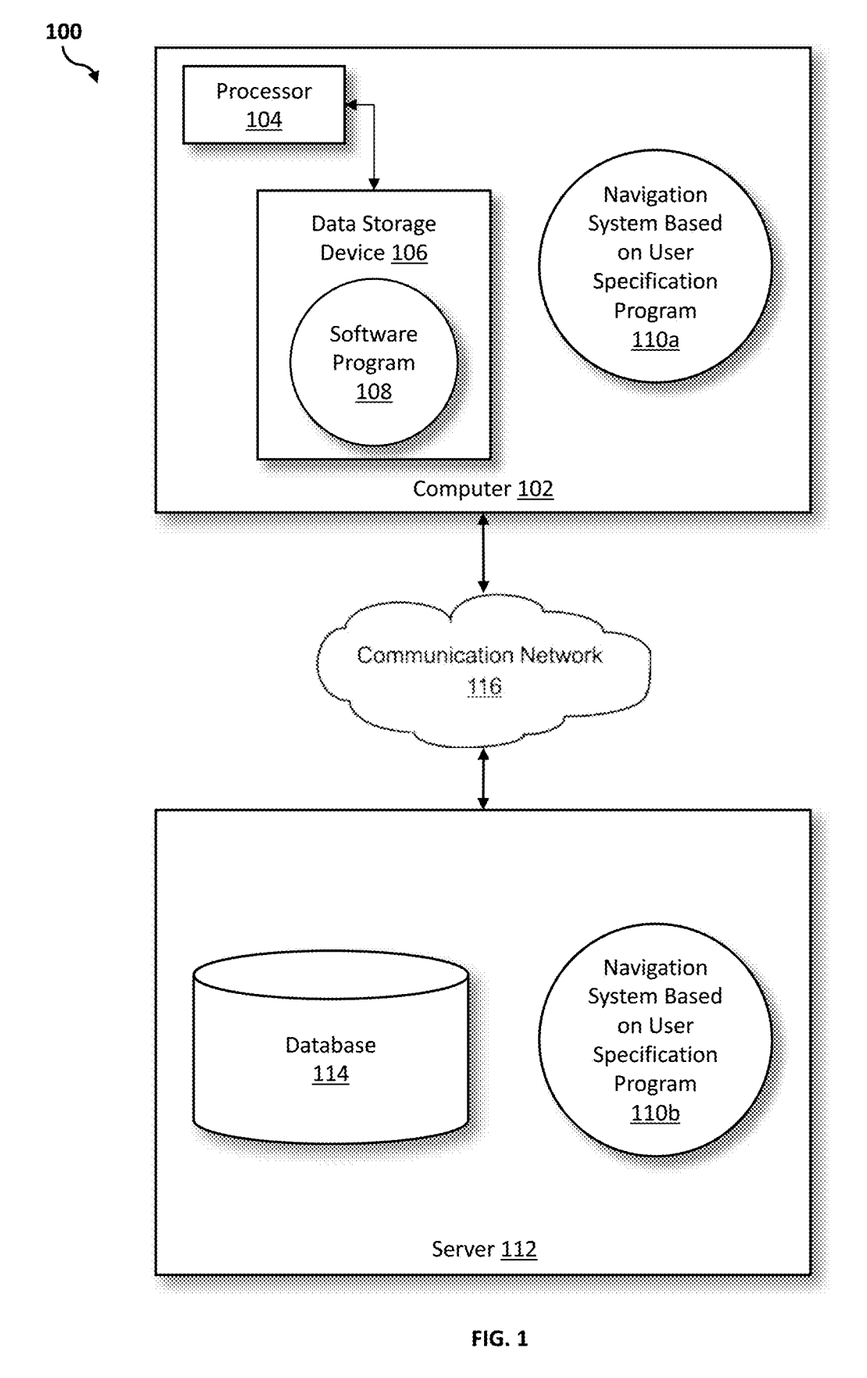
FIG. 1 illustrates a networked computer environment according to at least one embodiment.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a navigation system based on user specification program 110a. The networked computer environment 100 may also include a server 112 that is enabled to run a navigation system based on user specification program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the navigation system based on user specification program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the navigation system based on user specification program 110a, 110b (respectively) to connect to a store's inventory of items and to receive a determination as to what items within the store will be a good match for the user, based on a series of inputted user specifications. The navigation system based on user specification method is explained in more detail below with respect to FIGS. 2 and 3.

Figure 2:
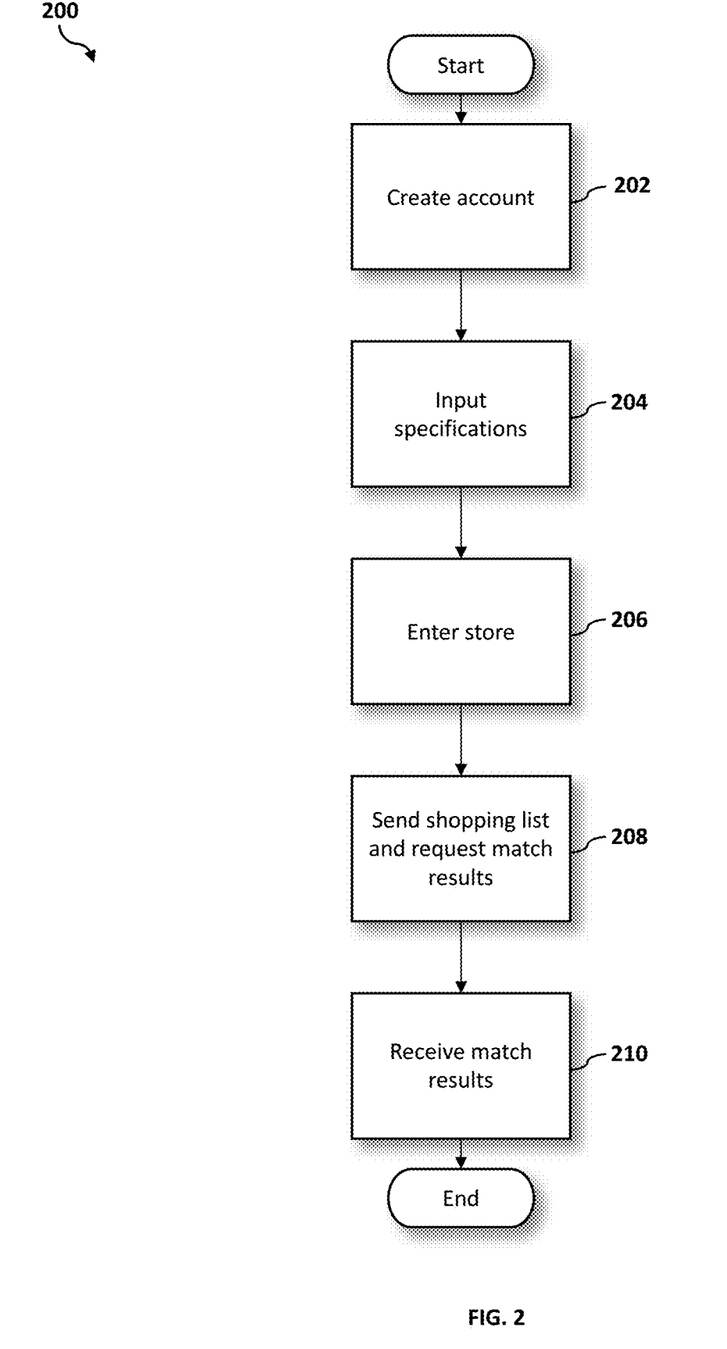
FIG. 2 is an operational flowchart illustrating a process for the navigation system based on user specification program according to at least one embodiment.

Referring now to FIG. 2, an operational flowchart illustrating the exemplary navigation system based on user specification process 200 used by the navigation system based on user specification program 110a and 110b according to at least one embodiment is depicted.

At 202, a user creates an account. At this step, a user may download the navigation system based on user specification program 110a, 110b and may register the user's mobile device, tablet, and/or any internet connected device with the navigation system based on user specification program 110a, 110b. Registration of a user's mobile device or tablet may include setting permissions within the navigation system based on user specification program 110a, 110b, including but not limited to enabling the navigation system based on user specification program 110a, 110b to gather location information picked up by the mobile device or tablet's location services (including but not limited to global positioning system location, and WLAN identifier, among other means of determining location). As will be described in more detail below, the navigation system based on user specification program 110a, 110b may utilize location services data from the user's mobile device or tablet to determine when a user enters a participating store (i.e., a store participating in the navigation system based on user specification program 110a, 110b).

The navigation system based on user specification program 110a, 110b, including the created user account, may be located on a cloud-based system, which may be accessed by a mobile device, tablet, computer, or any other internet-connected device. The user account may include shopping lists generated by the user, as well as preferred stores, among other things.

A user account may be an individual account, may be shared amongst one or more individuals (i.e., a shared user account), or may be shared amongst an entire family (i.e., a family account). All users of a shared user account may enter shopping lists within the shared user account. Therefore, a single shopping list may be shared between multiple devices and/or a single device may display multiple shopping lists. This may be accomplished by utilizing a shared cloud storage solution, as described previously. Shopping lists created within a shared user account may include specifications of all members of the shared group, or may be specific to the wants and needs of the individual user.

Individual users of a shared account may indicate personal allergies within the user account, and may further indicate the members of the shared account that may be consuming the purchased food, so that the specified allergies of each individual user may be respected.

Individual users of a shared account may also, optionally, create private shopping lists that may not be viewed by all other users of the shared account. Individual users of a shared account may also, optionally, create semi-private shopping lists that may be viewed by members of the shared account indicated by the creator of the shopping list. An individual user of a shared account may create a private shopping list to input personal items desired for purchase which the individual user does not wish to share with all members of the shared account.

Individual users of a shared account may also, optionally, create one or more user accounts which may be utilized for different purposes. For example, a user may share an account with family members and may share another, independent, account with roommates and/or colleagues. The user may view all personal and/or shared accounts in the interface of the navigation system based on user specification program 110a, 110b on the user's mobile device or tablet and the user may be logged in to multiple accounts at once. The user may toggle between accounts within the navigation system based on user specification program 110a, 110b interface.

For example, members of a large family may have varying health requirements (e.g., allergies). Therefore, for a single member of a large family to purchase food items for multiple members of the family, the single member may specify within the navigation system based on user specification program 110a, 110b each member of the family that is intending on consuming the purchased food, so that the navigation system based on user specification program 110a, 110b may respect the allergies of each consuming member.

Simultaneously to the user's registration (i.e., account creation) with the navigation system based on user specification program 110a, 110b, participating stores may create store accounts within the navigation system based on user specification program 110a, 110b wherein an inventory of the store's items and their respective locations within the store (e.g., aisle and shelf information) may be inputted. The nutritional content of the store's items may also be inputted into the navigation system based on user specification program 110a, 110b based on details included on the item's packaging. If an item is produced within the store, then details of the item's ingredients and the amount of each ingredient may not be gathered from a nutritional label, but may be provided by the store.

At 204, a user inputs specifications. Within the created user profile, as described previously at 202, a user may define one or more shopping lists with items that the user wishes to purchase (i.e., a shopping list), as well as defining a list of ingredients that the user wishes to avoid or to limit the intake of (i.e., a limit list). A user may further indicate within the navigation system based on user specification program 110a, 110b that the user has existing allergies and/or discomforts with certain food items. Specifications on the user's inputted shopping list may also include the number of ingredients comprising a given food item as a user may desire to limit the number of ingredients that comprise a single item.

A list comprising medical history of the user may also be provided within the user's account (i.e., a medical list), which may enable the navigation system based on user specification program 110a, 110b to make predictions on potential allergies or irritants of the individual, based on allergies and irritants which were specified within the user profile.

As described previously, a user may define one or more shopping lists within the created user profile. Shopping lists may be intended on serving different purposes (e.g., holiday party, Christening, etc.) and may be labeled accordingly within the navigation system based on user specification program 110a, 110b. Defined shopping lists may be shared across multiple devices or may be shared among multiple users of a shared user account. The user may not need to define an item's brand on a created user shopping list, and may instead opt to define a general category of item that the user wishes to purchase.

For example, a user may indicate on the user's shopping list that the user wishes to purchase granola bars. If the user also specifies within the user's profile that the user has an allergy to peanuts, then the navigation system based on user specification program 110a, 110b may narrow down the resulting list of applicable in-store items based on the user's indication of a desire to purchase granola bars, and also based on the user's allergy to peanuts. The resulting list may reflect specifications included in the user's profile, as well as availability of items for within the target store.

As will be discussed in more detail below, once the user enters a store, the navigation system based on user specification program 110a, 110b may identify suitable items for the user to purchase based on the user's predefined specifications, and may further provide a map of the store's interior, highlighting the items that the user desires to purchase along with those items' locations.

As described previously, user inputted specifications may include, among other things, a shopping list with ingredients and/or components of a desired item. Each ingredient (e.g., almonds, coconut, and/or sugar, among many other ingredients) on the shopping list may further have a corresponding maximum amount value. A maximum amount value may be a percentage value ranging from 0 to 100, inputted by the user of the navigation system based on user specification program 110a, 110b, and defining the amount of the ingredient desired by, or deemed acceptable to, the user. With respect to components of an item (e.g., preservatives, artificial colorings, and/or dairy, among other components), a 0 or 1 value may be utilized to indicate absence or presence, respectively, of the component within the item.

A user may specify whether an ingredient is absent or present in a food item by indicating a 0 or 1 next to each ingredient in the user profile, which may reflect an absence or presence of the ingredient in the food item. A user may optionally enter a percentage value next to a food ingredient or category, corresponding to the amount of the ingredient or category the user wishes a food item to be comprised of. A user may optionally enter a percentage value next to a specified nutrient, indicating the percent of daily intake of the nutrient the user wishes to ingest in the chosen food item. Alternatively, a user may provide a minimum value indicating the minimum amount of an ingredient, nutrient, vitamin, and/or category (e.g., protein, sugar, etc.), among other user specifications, that the user wishes to ingest.

At 206, a user enters a store. As described previously, upon a user's physical entrance into the store, a user may scan a quick response (i.e., QR) code within the store and/or utilize the location services data stored within the user's mobile device or tablet to recognize that the user has entered the store. If location services data is utilized, the navigation system based on user specification program 110a, 110b may be automatically updated with every change in location of the user's mobile device or tablet. Alternatively, a user of the navigation system based on user specification program 110a, 110b may send a current location from the user's location services data stored within the user's mobile device or tablet each time the user launches the navigation system based on user specification program 110a, 110b on a mobile device or tablet.

A QR code may be an image that contains a block of data and may prevent a user from needing to type the user's location manually within the navigation system based on user specification program 110a, 110b. A QR code may contain information, such as a URL or credentials or authorization codes, so that once a user scans the QR code, upon entrance into a store, the user side of the navigation system based on user specification program 110a, 110b (i.e., a client application) can connect to the store side of the navigation system based on user specification program 110a, 110b (i.e., a server application) and the data on the store's server can be accessed by a user. By using a QR code, a user's mobile device or tablet running the navigation system based on user specification program 110a, 110b may ensure that there is proper connectivity to the server which corresponds to the store that the user is present in. Alternatively, a user of the navigation system based on user specification program 110a, 110b may connect to the store's server via Bluetooth® (Bluetooth and all Bluetooth-based trademarks and logos are trademarks or registered trademarks of Bluetooth SIG, Inc. and/or its affiliates) connection.

For data uploaded by a store to be accessible by a user, there may be both a client component and a server component of the navigation system based on user specification program 110a, 110b. The client component may be an application loaded on a user's device, as described previously, and the server component may be a connection to a store's server. A store participating in the navigation system based on user specification program 110a, 110b may load the food items and inventory currently for sale onto a server which is connected to the navigation system based on user specification program 110a, 110b. The information pertaining to the food items and inventory placed on the server by the store may include location information of an item, including the aisle location and shelf location of items located within the store. A user of the navigation system based on user specification program 110a, 110b may thereafter retrieve loaded data from the server upon entrance into a participating store.

At 208, a user sends a shopping list and requests match results. Generating food matches between items included on the user's list of inputted specifications and items available for purchase within the store entails utilizing comparison algorithms (e.g., string comparison, among others).

The navigation system based on user specification program 110a, 110b may compare strings correlating to an ingredient and/or component of a food item. For example, a user of the navigation system based on user specification program 110a, 110b may indicate (i.e., specify) a desire to purchase whole wheat bread which is comprised of less than three percent sugar. When the user enters a store, the user may scan a QR code, or may send location services data stored within the user's mobile device or tablet to the navigation system based on user specification program 110a, 110b, as described previously at 206, so that the navigation system based on user specification program 110a, 110b may determine what store the user has entered and may access the correct store server. Next, the user may send inputted user specifications to the navigation system based on user specification program 110a, 110b so that the program may provide a list of products suitable for purchase within the store. In determining what products may be suitable for the user, the navigation system based on user specification program 110a, 110b may compare each user inputted specification to the specifications of each item of the desired type available for purchase within the store.

The navigation system based on user specification program 110a, 110b may be connected to one or more external databases (i.e., database 114), including a food database (i.e., database 114) and a medical database (i.e., database 114) of food and medical information which may be utilized to provide suggestions to a user on other foods to avoid based on indicated food specifications, food allergies, and/or food discomforts. The food database 114 and medical database 114 may be maintained on servers which are connected to and accessible by the navigation system based on user specification program 110a, 110b, but are located independent from the user's device. The food database 114 and medical database 114 may contain data inputted by numerous sources, including but not limited to doctors, health professionals, and registered dieticians, among other sources. The food database 114 and medical database 114 may also contain food and medical data obtained from the internet. The food database 114 may include food information including composition and ingredients of food, among other information. The medical database 114 may contain medical information pertaining to allergies, diseases, illnesses, and symptoms, among other things. The medical database 114 may further contain information necessary to diagnose, treat, and prevent the aforementioned allergies, diseases, and illnesses.

For example, if a user provides an indication of a desire to avoid bread, based on an underlying discomfort with gluten, the navigation system based on user specification program 110a, 110b may utilize the food database 114 to recognize that pasta also contains gluten, and that the user may wish to avoid pasta as well. Alternatively, if a user provides an indication (e.g., within an inputted medical list within the navigation system based on user specification program 110a, 110b) of a shellfish allergy to crustaceans (e.g., shrimp, crab, and lobster), the navigation system based on user specification program 110a, 110b may utilize the medical database 114 to determine that the user may also have a shellfish allergy to mollusks (e.g., clams, mussels, oysters) and may avoid these foods as well.

Additionally, a store may utilize data analytics to analyze requests sent by users of the navigation system based on user specification program. Requests for food items sent by users of the navigation system based on user specification program 110a, 110b may be saved and stored by the store receiving the request, enabling the store to use the request to assist with purchasing and stocking of items in the future. The requests received from all users of the navigation system based on user specification program 110a, 110b may be compiled and analyzed to assist in future purchasing. Additionally, as a precondition to use of the navigation system based on user specification program 110a, 110b, a user may be prompted to permit the anonymized (e.g., exclusive of any identification) retrieval of the user's shopping list by the store in which the user is shopping. A user may, optionally, permit the store to retrieve identifying information from the user's account, including age and gender, to permit the store to analyze the purchase patterns of shoppers based on demographic.

At 210, a user receives the match results. A resulting map and list of item locations may be sent to a user of the navigation system based on user specification program 110a, 110b within the program interface. A resulting map and list of item locations may additionally or alternatively, at the option of the user, be sent via email. The navigation system based on user specification program 110a, 110b may also provide an optimized route to one or more stores that the user wishes to visit, which may enable the user to purchase the list of desired items in the fastest amount of time and/or in the most inexpensive and affordable way.

A user may access the navigation system based on user specification program 110a, 110b from the user's mobile device, tablet, and/or any other internet connected device to provide a list of items desired to be purchased, as well as stores desired to be visited. The user may upload the generated lists to the navigation system based on user specification program 110a, 110b and may request from the navigation system based on user specification program 110a, 110b an optimized route to visit the desired stores and to purchase the items from the user's list. The user may be emailed a portable document format file (PDF) of the optimized list from the navigation system based on user specification program 110a, 110b and may also, optionally, print a physical copy of the PDF, which the user may carry on the optimized route. The optimized list may include each item on the user's desired food list, the nearest store in which the item is sold, the store which is selling the item for the lowest price, and the quantity of the item which is available for sale within each listed store. The optimized list generated by the navigation system based on user specification program 110a, 110b may further contain a preferred order of travel so that the user may purchase all items on the list in the fastest and most efficient (e.g., least amount of distance, etc.) way. The user may specify within the user profile an optimization preference including whether the user wishes to spend the least amount of time or money, among other optimization preferences.

If a user is using a mobile device or tablet, then the user may additionally or alternatively, at the option of the user, utilize step-by-step navigation provided within the interface of the navigation system based on user specification program 110a, 110b on the user's mobile device or tablet. The step-by-step navigation may guide the user through the store to the aisle and shelf of each item on the user's purchase list, based on the store's connected server which houses location information, as described previously.

Figure 3:
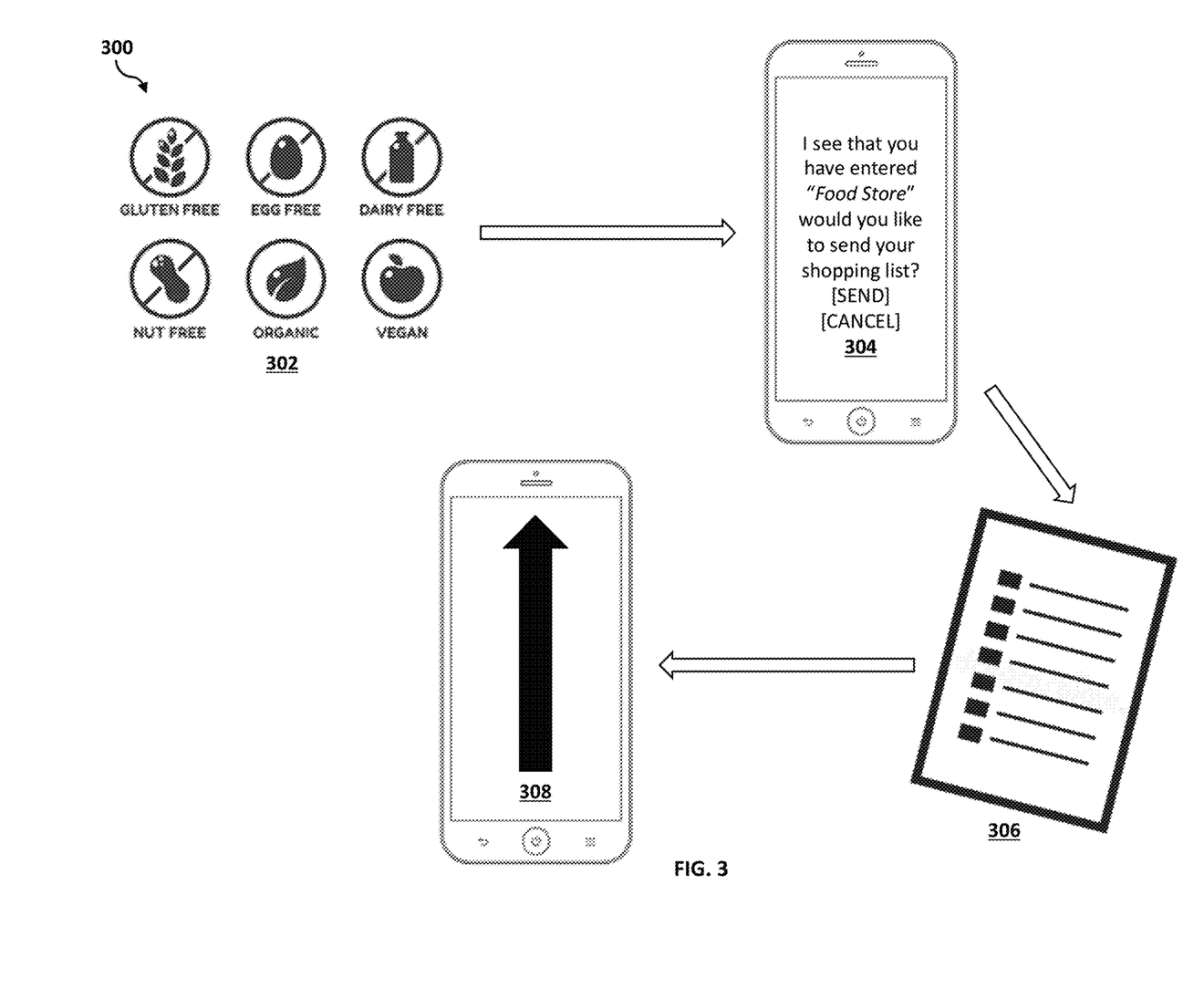
FIG. 3 is an exemplary illustration of an in-store navigation scenario according to at least one embodiment.

Referring now to FIG. 3, an exemplary illustration of an in-store navigation scenario 300 according to at least one embodiment is depicted. A user Camila downloads the navigation system based on user specification program 110a, 110b on her mobile device and creates a user profile, as described previously at 202. Camila's user profile includes multiple specifications 302, as described previously at 204, including Camila's medical history of treatment for celiac disease, preference to purchase gluten free, nut free, egg free, dairy free, organic, and vegan products, and a personal shopping list of chocolate chip cookies, berries, and pasta. Camila also provides her home address, around which she will most frequently be shopping, as well as a list of preferred stores. Camila's top choice for purchasing food items is a health food store located one mile from Camila's home. Camila has indicated within her user profile that a top preference for route optimization is proximity, though Camila rates cost as her second most important consideration.

Camila drives to her preferred food store and scans the store's QR code so that the navigation system based on user specification on Camila's mobile device can communicate with the database (i.e., database 114) of product information provided by the store, as described previously at 206. At 304, Camila is prompted to send her shopping list to the navigation system based on user specification program 110a, 110b. Knowing where Camila is shopping, the navigation system based on user specification program 110a, 110b will compare the food items present within the store to the food items desired by Camila, as described previously at 208.

The navigation system based on user specification program 110a, 110b compares the items on Camila's list to the items available for purchase within the store, as described previously at 208. Once suitable food matches are found, which reflect Camila's gluten allergy and desired food items, a match list will be provided to Camila, as described previously at 210.

A list of match results 306 is provided to Camila's mobile device within the navigation system based on user specification program 110a, 110b interface. Camila opts to receive a step-by-step navigation guide 308 to assist Camila in locating desired items. Audio and visual assistance projects on and from Camila's mobile device guiding Camila around the store and directly to each desired item.

It may be appreciated that FIGS. 2 and 3 provide only an illustration of one embodiment and do not imply any limitations with regard to how different embodiments may be implemented. Many modifications to the depicted embodiment(s) may be made based on design and implementation requirements.

Figure 4:
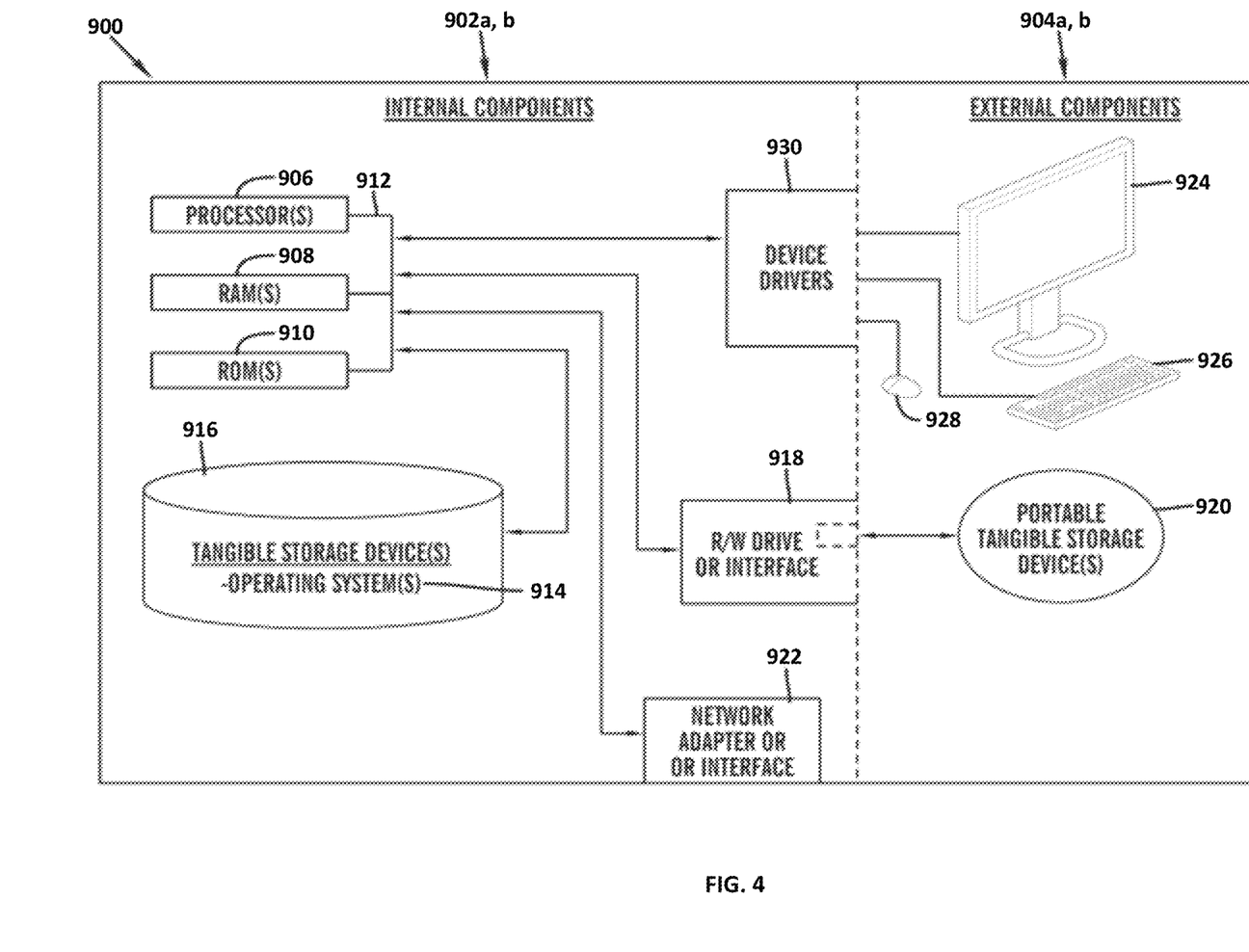
FIG. 4 is a block diagram of internal and external components of computers and servers depicted in FIG. 1 according to at least one embodiment.

FIG. 4 is a block diagram 900 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 4. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the navigation system based on user specification program 110a in client computer 102, and the navigation system based on user specification program 110b in network server 112, may be stored on one or more computer-readable tangible storage devices 916 for execution by one or more processors 906 via one or more RAMs 908 (which typically include cache memory). In the embodiment illustrated in FIG. 4, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the navigation system based on user specification program 110a and 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the navigation system based on user specification program 110a in client computer 102 and the navigation system based on user specification program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the navigation system based on user specification program 110a in client computer 102 and the navigation system based on user specification program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
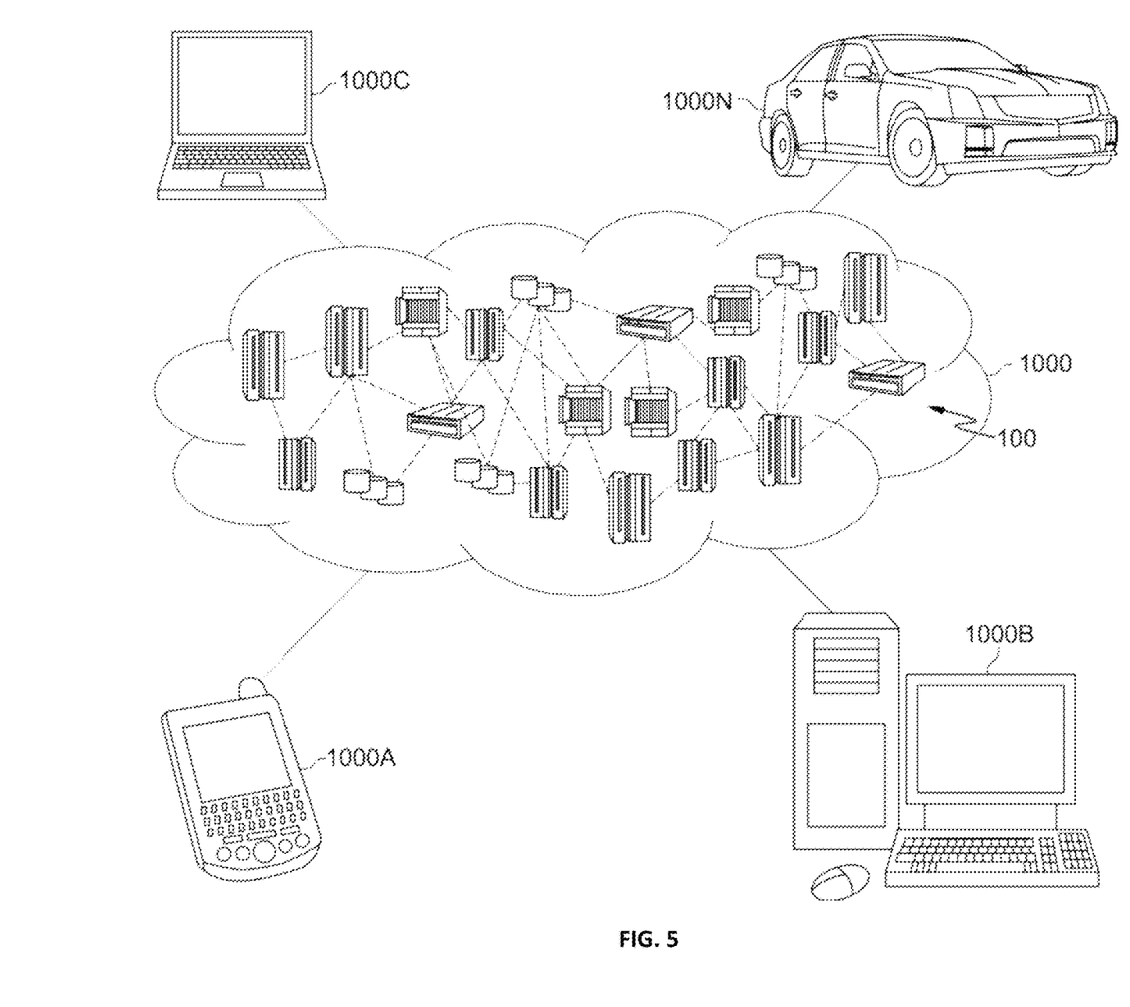
FIG. 5 is a block diagram of an illustrative cloud computing environment including the computer system depicted in FIG. 1, in accordance with an embodiment of the present disclosure.

Referring now to FIG. 5, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 5 are intended to be illustrative only and that computing nodes 100 and cloud computing environment 1000 can communicate with any type of computerized device over any type of network and/or network addressable connection (e.g., using a web browser).

Figure 6:
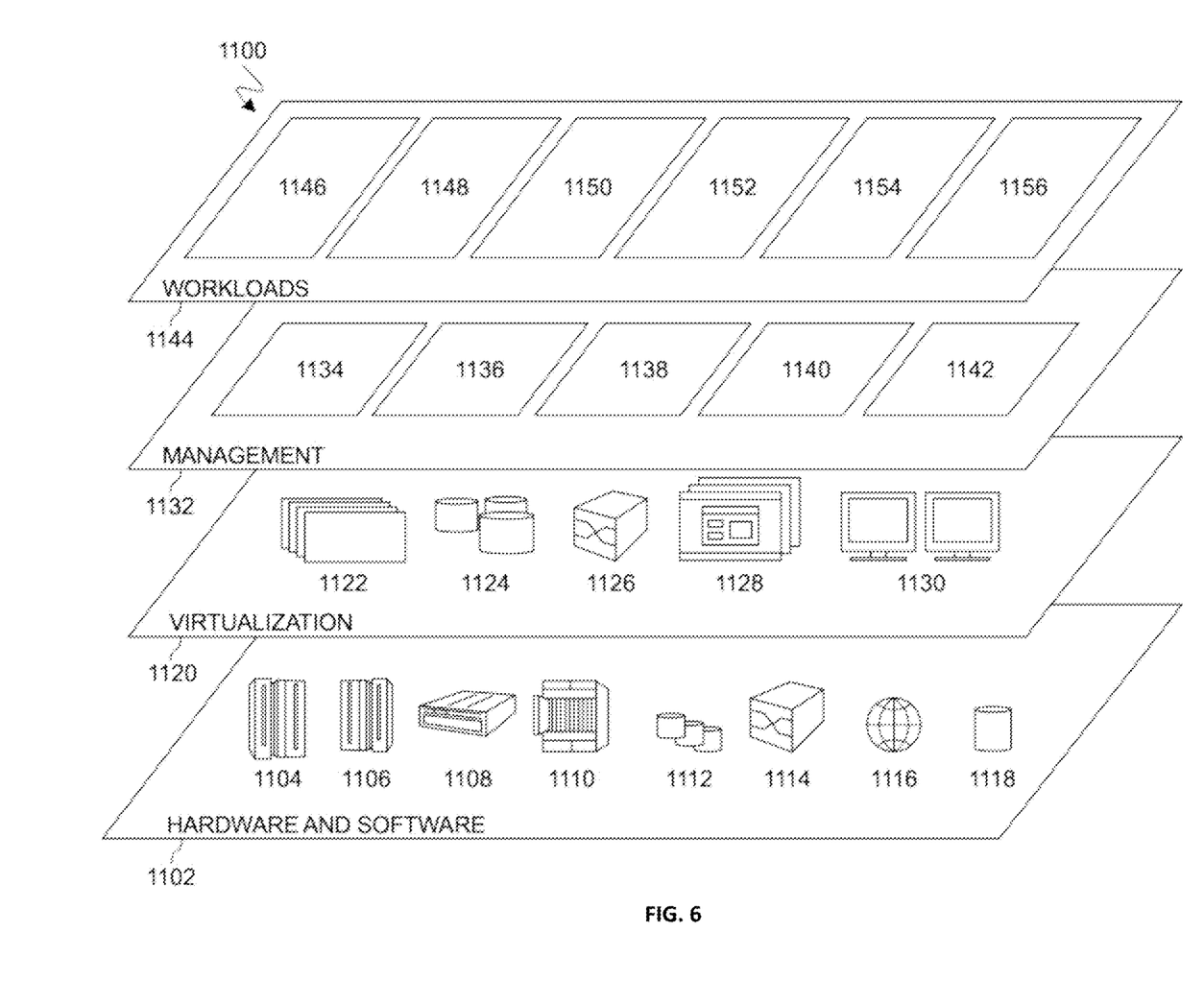
FIG. 6 is a block diagram of functional layers of the illustrative cloud computing environment of FIG. 5, in accordance with an embodiment of the present disclosure.

Referring now to FIG. 6, a set of functional abstraction layers 1100 provided by cloud computing environment 1000 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and navigation system based on user specification 1156. A navigation system based on user specification program 110*a*, 110*b* provides a way to improve the technical field of navigation systems by connecting to a store's inventory of items and determining, based on inputted user specifications, what items within the store will be a good match for the user.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of providing digital navigation to a user on a user device, the method comprising:
using a global positioning system (GPS) location and a WLAN identifier to determine a location of the user device based on a user-scanned QR code, wherein the GPS location and the WLAN identifier comprise the user device's location services, and wherein configuring permissions within the user device enable the method to gather any location information picked up by the user device's location services after the method is launched and while the method is active;
automatically updating the location of the user device with every change in location of the user device based on the GPS location and the WLAN identifier;
communicating a plurality of navigation commands to the user, on the user device, for navigation within a store, wherein the plurality of navigation commands are generated in response to the determined location of the user device and further based on a user-provided specification, wherein the user-provided specification is linked to an account of the user, and wherein the account of the user is selected from the group consisting of an individual account, a shared account, and a family account,
wherein the shared account and the family account utilize a cloud computing environment to share a shopping list between multiple devices, wherein the shopping list includes at least one specification and at least one health requirement of each of a plurality of members of a shared group, wherein the at least one specification of one of the plurality of members of the shared group includes a general category of item that the one of the plurality of members of the shared group wishes to purchase, as well as a percentage value of a food ingredient which may be present in the list of items to be purchased, and wherein the at least one specification and the at least one health requirement of each of the plurality of members must be satisfied when generating the optimized route; and
sending, to the user, an optimized route to one or more stores, based on the user-provided specification and the automatically updated location of the user device, wherein the optimized route includes a list of items to be purchased which both satisfy the user-provided specification and a preference to spend a least amount of money.

2. The method of claim 1, wherein the user-provided specification is selected from the group consisting of a shopping list, a limit list, and a medical list.

3. The method of claim 1, further comprising:
connecting to an inventory list maintained on a server located independent from the user device, wherein the inventory list maintained on the server includes a location of an item.

4. The method of claim 1, further comprising:
receiving a user request for a match result based on the user-provided specification, the user-scanned QR code.

5. The method of claim 1, wherein the plurality of navigation commands are auditory commands and visual commands.

6. The method of claim 1, further comprising:
connecting to a medical database maintained on a server located independent from the user device, wherein the medical database includes diagnosis, treatment, and prevention data;
connecting to a food database maintained on a server located independent from the user device, wherein the food database includes composition of food data and ingredient of food data; and
utilizing the medical database and the food database to provide a suitable product based on the user-provided specification.

7. The method of claim 1, further comprising:
prompting the user to permit a retrieval of the user's data by the store;
upon receiving approval from the user to permit the retrieval of the user's data by the store, anonymizing the user-inputted specification; and
sending the anonymized user-inputted specification to a connected store server for data analytics.

8. A computer system for providing digital navigation to a user on a user device, comprising:
one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
using a global positioning system (GPS) location and a WLAN identifier to determine a location of the user device based on a user-scanned QR code, wherein the GPS location and the WLAN identifier comprise the user device's location services, and wherein configuring permissions within the user device enable the method to gather any location information picked up by the user device's location services after the method is launched and while the method is active;
automatically updating the location of the user device with every change in location of the user device based on the GPS location and the WLAN identifier;
communicating a plurality of navigation commands to the user, on the user device, for navigation within a store, wherein the plurality of navigation commands are generated in response to the determined location of the user device and further based on a user-provided specification, wherein the user-provided specification is linked to an account of the user, and wherein the account of the user is selected from the group consisting of an individual account, a shared account, and a family account,
wherein the shared account and the family account utilize a cloud computing environment to share a shopping list between multiple devices, wherein the shopping list includes at least one specification and at least one health requirement of each of a plurality of members of a shared group, wherein the at least one specification of one of the plurality of members of the shared group includes a general category of item that the one of the plurality of members of the shared group wishes to purchase, as well as a percentage value of a food ingredient which may be present in the list of items to be purchased, and wherein the at least one specification and the at least one health requirement of each of the plurality of members must be satisfied when generating the optimized route; and sending, to the user, an optimized route to one or more stores, based on the user-provided specification and the automatically updated location of the user device, wherein the optimized route includes a list of items to be purchased which both satisfy the user-provided specification and a preference to spend a least amount of money.

9. The computer system of claim 8, wherein the user-provided specification is selected from the group consisting of a shopping list, a limit list, and a medical list.

10. The computer system of claim 8, further comprising:
connecting to an inventory list maintained on a server located independent from the user device, wherein the inventory list maintained on the server includes a location of an item.

11. The computer system of claim 8, further comprising:
receiving a user request for a match result based on the user-provided specification and the user-scanned QR code.

12. The computer system of claim 8, wherein the plurality of navigation commands are auditory commands and visual commands.

13. A computer program product for providing digital navigation to a user on a user device, comprising:
one or more computer-readable storage media and program instructions stored on at least one of the one or more tangible storage media, the program instructions executable by a processor to cause the processor to perform a method comprising:
using a global positioning system (GPS) location and a WLAN identifier to determine a location of the user device based on a user-scanned QR code, wherein the GPS location and the WLAN identifier comprise the user device's location services, and wherein configuring permissions within the user device enable the method to gather any location information picked up by the user device's location services after the method is launched and while the method is active;
automatically updating the location of the user device with every change in location of the user device based on the GPS location and the WLAN identifier;
communicating a plurality of navigation commands to the user, on the user device, for navigation within a store, wherein the plurality of navigation commands are generated in response to the determined location of the user device and further based on a user-provided specification, wherein the user-provided specification is linked to an account of the user, and wherein the account of the user is selected from the group consisting of an individual account, a shared account, and a family account,
wherein the shared account and the family account utilize a cloud computing environment to share a shopping list between multiple devices, wherein the shopping list includes at least one specification and at least one health requirement of each of a plurality of members of a shared group, wherein the at least one specification of one of the plurality of members of the shared group includes a general category of item that the one of the plurality of members of the shared group wishes to purchase, as well as a percentage value of a food ingredient which may be present in the list of items to be purchased, and wherein the at least one specification and the at least one health requirement of each of the plurality of members must be satisfied when generating the optimized route; and
sending, to the user, an optimized route to one or more stores, based on the user-provided specification and the automatically updated location of the user device, wherein the optimized route includes a list of items to be purchased which both satisfy the user-provided specification and a preference to spend a least amount of money.

14. The computer program product of claim 13, wherein the user-provided specification is selected from the group consisting of a shopping list, a limit list, and a medical list.

* * * * *